United States Patent [19]
Hack et al.

[11] Patent Number: 5,431,819
[45] Date of Patent: Jul. 11, 1995

[54] PROCESS FOR THE BIOLOGICAL TREATMENT OF SOLID ORGANIC MATERIAL

[75] Inventors: Petrus J. F. M. Hack, DT Balk; Sjoerd H. J. Vellinga, CP Tjalleberd, both of Netherlands

[73] Assignee: Paques B.V., Balk, Netherlands

[21] Appl. No.: 81,281

[22] PCT Filed: Jan. 14, 1992

[86] PCT No.: PCT/NL92/00007
§ 371 Date: Jun. 25, 1993
§ 102(e) Date: Jun. 25, 1993

[87] PCT Pub. No.: WO92/13084
PCT Pub. Date: Aug. 6, 1992

[30] Foreign Application Priority Data
Jan. 15, 1991 [NL] Netherlands .................. 9100063

[51] Int. Cl.$^6$ ........................................ C02F 11/04
[52] U.S. Cl. .............................. 210/603; 210/610; 210/631
[58] Field of Search ............... 210/603, 605, 610, 611, 210/620–626, 630, 631

[56] References Cited

U.S. PATENT DOCUMENTS 4,318,993 3/1982 Ghosh et al. .................. 210/631
4,384,956 5/1983 Mulder ........................... 210/605
4,915,840 4/1990 Rozich ............................ 210/605

FOREIGN PATENT DOCUMENTS 0142873 5/1985 European Pat. Off. .
0159054 10/1985 European Pat. Off. .
0170332 2/1986 European Pat. Off. .

OTHER PUBLICATIONS

"High Rate Two-Phase for the Anaerobic Degradation of Cellulose, Employing Rumen Microorganisms for an Efficient Acidogenesis", *Biotechnology and Bioengineering*, vol. 31, 1988, By H. Gijzen et al., pp. 418–425.

Primary Examiner—Thomas S. Wyse
Attorney, Agent, or Firm—Young & Thompson

[57] ABSTRACT

The invention relates to a process for the biological treatment of essentially solid organic material, such as fruit, vegetable and garden waste, wherein the material is successively treated in a hydrolysis tank and in an anaerobic methane reactor, and at least a part of the solids issuing from the hydrolysis tank is treated in a second anaerobic reactor with at least one a microorganism of the rumen flora of ruminants; the liquid soluble material produced in the second reactor is further treated in the methane reactor. The material is preferably pretreated mechanically in a destructor. The invention furthermore provides an apparatus for carrying out this process.

8 Claims, 1 Drawing Sheet

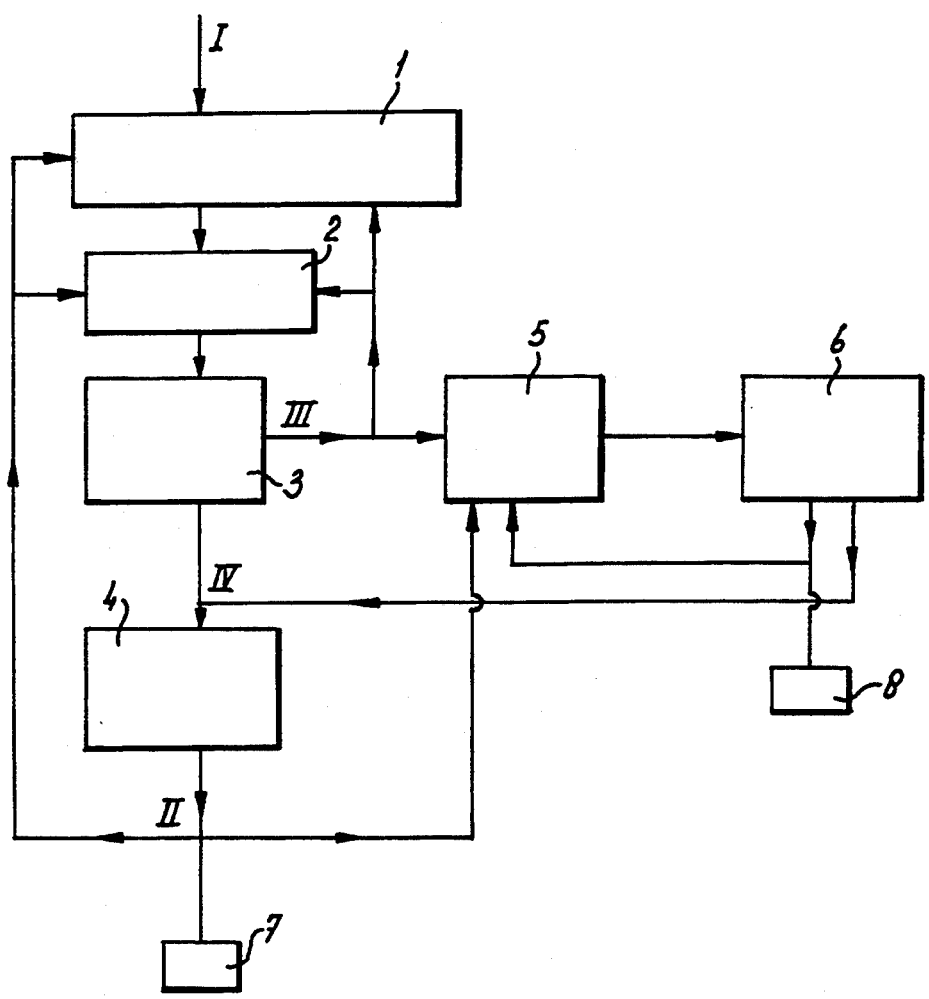

PROCESS FOR THE BIOLOGICAL TREATMENT OF SOLID ORGANIC MATERIAL

FIELD OF THE INVENTION

The present invention relates to a process for the biological treatment of essentially solid organic material, wherein the material is successively subjected to a hydrolysis treatment and an anaerobic fermentation.

BACKGROUND OF THE INVENTION

Several types of treatment systems for solid biological waste are presently being developed. These systems should make it possible, firstly to obtain a stabilized and sanitarily reliable end product which can be used for example as compost or soil improver, and secondly to obtain a volume reduction, making dumping less expensive. The types of waste that can be treated using such treatment systems include:

separately collected fruit, vegetable and garden waste;
the organic fraction of household refuse (RDF or wet fraction) from a household refuse treatment plant;
material withdrawn from auctions;
cuttings of verges, trimming waste and the like;
catering waste.

The biological systems can be divided into aerobic and anaerobic systems. An aerobic system is concerned with conventional composting and improvements thereof. Anaerobic systems can be divided into anaerobic fermentation (30°–40° C.), thermophilic fermentation (55°–65° C.) and two-stage systems. Anaerobic fermentation and thermophilic fermentation are processes wherein the entire waste flow is treated, without differentiating between the residence time for liquids and the residence time for solids in the system. Such systems are mostly single-stage and they can be applied both as a completely mixed system or in a plug stream reactor. A disadvantage of these systems is the relatively long treatment time (residence time) and the resulting necessity of large and expensive equipment.

In a two-stage process as defined in the preamble, the selected residence time of the solid material can be longer than the residence time of the liquid and, moreover, different biological reactions can be carried out in different parts of a plant.

A process according to the preamble is known, for example from European patent applications 37612 and 142873. According to EP-A-37612 solid organic material is subjected to a two-stage anaerobic treatment, whereby the material is decomposed into mainly lower fatty acids and other water soluble substances, carbon dioxide, methane and a residual fraction in the first stage, and the water soluble substances and the fatty acids are treated in a second stage leading to formation of methane and carbon dioxide. According to EP-A-142873 the solid material resulting from the first stage (hydrolysis/acidification) is partly recycled and the liquid is treated in a methane reactor in the second stage.

An advantage of these known systems is the relative simplicity of the necessary equipment and of the execution of the process. A disadvantage, however, is that no advanced degree of degradation and thus no substantial volume reduction can be achieved for many types of waste, and thus the cost of dumping is not notably reduced.

A process for the production of methane from solid vegetable waste, wherein the vegetable material is treated with ciliates (microorganisms such as present in the rumen of ruminants) and methane bacteria in a liquid medium, is known from European patent application 159054. The liquid thus obtained can be treated in a separate anaerobic reactor wherein additional methane is produced. Such a method which is thus based on the use of the rumen flora of ruminants, is also known as the so-called RUDAD system (RUmen Derived Anaerobic Digestion).

The RUDAD system has the advantage that waste also containing components that are difficult to degrade can be degraded to a large extent and can thus be considerably reduced in volume. A disadvantage is however that the process should be carefully controlled and that fluctuations of the quantities and nature of the waste supply as occurring in practice disturb the process stability to the extent that an effective waste degradation is no longer achieved.

The problem of fluctuations of the supply could in principle be solved by using a large equalizing buffering tank, but this does not solve the problem of rapid acidification of the easily degradable part of the waste (production of acetic and propionic acid). This acidification not only results in stench and lowering of the pH, but also inhibits the biological processes, in particular of the rumen derived flora, when concentrations become excessively high, irrespective of the pH. Such a high concentration of acid components would require a high circulation rate in order to remove all organic acids produced from the rapidly acidifying material; this would results in very short hydraulic retention times of 2 to 4 hours in the RUDAD reactor, whereas a minimum retention time of 6 hours is necessary in order to maintain the desired biomass population, and the optimal hydraulic retention time is about 12 hours. Thus a stable operation of the RUDAD reactor is not possible.

SUMMARY OF THE INVENTION

An object of the present invention is to provide a process and an apparatus for the treatment of essentially solid organic material with the advantages of the known systems and concomitantly without their disadvantages.

This object is achieved by a process according to the preamble which is characterized in that at least a part of the material arising from the hydrolysis treatment is treated with at least one microorganism belonging to the rumen flora of ruminants.

The process of the invention allows a substantial part of the acidifying products to be produced in the prehydrolysis reactor. These can then be fed directly into the anaerobic reactor, without disturbing the rumen derived flora that is used to degrade the solid part of the waste. In this way, variations in waste supply can be accomodated easily while the process results in high biogas production and low amounts of residual solids, and is thus highly cost-effective.

Microorganisms belonging to the rumen flora of ruminants are predominantly ciliates. For the sake of brevity, such microorganisms are designated below as ciliates or as rumen microorganisms. Suitable microorganisms have been described in European patent application 159054. Suitable ciliates include the species *Eudiplodinium maggi, Diplodinium dentatum, Epidinium ecaudatum, Entodinium simplex, Entodinium longinudeatum, Entodinium caudatum, Dasytrichia ruminantium* and *Isotricha prostoma*.

The part of the material that is subjected to the treatment with ciliates comprises at least a part of the solid material and preferably all coarse solids issuing from the preceding hydrolysis treatment.

Preferably, a part of the solids derived from the hydrolysis treatment is recycled to the hydrolysis treatment, so that the residence time of the solids during the hydrolysis treatment is greater than that of the liquid, and thus a more efficient degradation takes place. Similarly, the solids issuing from the treatment with the ciliates are preferably partly recycled to the ciliate treatment, also resulting in a longer residence time for the solids than for the liquid.

Preferably the waste which is to be treated is pretreated in a destructor prior to the hydrolysis treatment, whereby the waste is mechanically reduced in size and mixed and optionally sieved. The waste material can also be diluted in this stage, preferably with the effluent of the anaerobic fermentation. The solid material that is subjected to the treatment with ciliates can also be diluted with a part of the anaerobic reactor effluent.

The present invention also relates to an apparatus for the treatment of essentially solid organic material, in particular organic waste, which is schematically depicted in the accompanying figure. The apparatus consists at least of a hydrolysis tank 2 having means for the supply of partly solid material and for the supply of diluting liquid, a separator 3 connected with the hydrolysis tank 2 for separating and recycling solid material, an anaerobic reactor 4 connected with the separator 3 for the anaerobic treatment of liquid material, an anaerobic reactor 5 connected with the separator 3 for the anaerobic treatment of partly solid material, and a separator 6 connected with the anaerobic reator 5 for separating and recycling solid material.

Preferably, the apparatus comprises a destructor 1 linked before the hydrolysis tank 2, wherein the waste can be reduced in size mechanically, homogenized and optionally sieved. The apparatus further preferably comprises conducts for recycling liquid from the anaerobic reactor 4 to the hydrolysis tank 2, the anaerobic reactor 5 and optionally the destructor 1. The anaerobic reactor 4 can be of any conventional type. A reactor according to the Upflow Anaerobic Sludge Blanket (UASB) system is preferred. The UASB system has been described by Lettinga et al., Anaerobic Digestion (D. A. Stafford, B. J. Wheatly and D. E. Huges, Ed.) Univ. Coll., Cardiff, Wales, 167–186, 1980). Also preferred is an anaerobic reactor according to the gas-lift system, which is provided with a rising pipe and a separator for separating solid and liquid material. Such a reactor has been described in European patent application 170332. The anaerobic reactor can also be in the form of a combination of two or more of such gas-lift reactors. The combination of the hydrolysis tank and anaerobic reactor 4 can be a two-stage system as described in European patent applications 37612 or 142873. The anaerobic reactor 5 for the treatment of partly solid material with rumen microorganisms can be a reactor as described in European patent application 159054.

BRIEF DESCRIPTION OF THE DRAWING

The process and the apparatus according to the invention can be described in more detail with reference to the accompanying figure.

DETAILED DESCRIPTION OF THE INVENTION

1) Mechanical destruction

The waste supplied through flow I is reduced in size and homogenized in the destructor 1. Undesirable materials which can disturb the biological processes or apparatus can also be removed. The supplied organic material can optionally be diluted with a liquid flow, preferably with a part of the effluent II of the anaerobic reactor.

2) Hydrolysis

The material obtained by the mechanical destruction is, optionally after sieving, supplied to the hydrolysis tank 2, wherein the organic material is subjected to microorganisms effecting hydrolysis and acidification. The enzymes of these microorganisms cause organic substances to be partly converted to smaller, water soluble substances, such as sugars, amino acids, fatty acids and alcohols. The pH of this system may vary between 4.5 and 7.5, while the optimum pH for these microorganisms is 5.5 to 6.5. In the hydrolysis tank 2 the waste can be present in a concentration of 20 to 150 kg per $m^3$, preferably 50–100 $kg/m^3$. This means that the waste flowing from the destructor 1 has to be diluted in many cases, for example with purified water derived from the anaerobic reactor 4. The temperature is preferably between 20° and 40° C. A precise control of the conditions in the hydrolysis reactor is not necessary. Under the conditions as indicated above, a microbial population predominantly consisting of acidifying and hydrolyzing bacteria is maintained.

3) Separation

The flow issuing from the hydrolysis tank 2 is separated in the separator 3 into a solid phase and a liquid phase. The solid material (III) consisting of material not yet or incompletely hydrolyzed is partly recycled to the mechanical destruction (1) and/or to the hydrolysis tank (2) and is further conducted to the anaerobic reactor 5. The separation of solids can optionally be effected in two stages: separation of the coarse solid fraction for example using a rotary sieve, said coarse fraction being recycled, and separation of the finer solids for example using a belt sieve.

4) Anaerobic reactor

The liquid flow IV issuing from the separator 3 with the organic substances dissolved therein is subjected to methane forming bacteria in the anaerobic reactor, whereby biogas (mainly methane and to a lesser extent carbon dioxide) is predominantly formed. The methane forming microorganisms in this reactor are relatively slowly growing microorganisms with an optimum pH of 7–8. The bacteria can for example be present on a supporting granulate. Biogas produced in the anaerobic reactor is suitable as a fuel: the liquid flow II arising from the anaerobic reactor is usually sufficiently purified to be discharged (7) without difficulty. A part of the liquid flow II can be used for diluting or adjusting the pH in the destructor 1, the hydrolysis tank 2 and/or the reactor 5. If desired, the liquid flow II can be further purified in an aerobic process (7).

5) Treatment with rumen derived flora

In the reactor 5, the conditions of the rumen of ruminants are simulated. The reactor 5 is fed with at least a part of the solid material III issuing from the separator 3. The temperature in the reactor 5 is preferably between 35° and 41° C., more preferably between 38° and 40° C., and the pH is preferably between 5.5 and 7, more preferably between 6.5 and 7. The concentration of solids is preferably between 40 and 120, more preferably between 50 and 100 kg/m$^3$. If necessary, the concentration of solids and/or the pH can be adjusted by adding aqueous phase derived from the anaerobic reactor 4. The pH can be adjusted further by addition of alkali. Under these conditions a varied microbial population consisting partly of bacteria, partly of fungi and ciliates capable of degrading most of the fibrous, cellulosic components of the waste is maintained. As is the case in the hydrolysis tank 2, different residence times for solid and liquid are used in the reactor 5, resulting in an optimal degradation of the solid waste. The flow issuing from the reactor 5 is separated to this effect and the solid fraction is partly recycled. The residence time for the solids is preferably 1–3 days.

6) Separation

The material originating from the reactor 5 is separated into a solid phase and a liquid phase in the separator 6. The liquid phase containing the dissolved organic substances produced in the reactor 5, is conducted to the anaerobic reactor 4, wherein the organic substances are further decomposed to methane gas and other products. The solids are partly recycled to the reactor 5 and are partly removed from the system for further processing, dumping, incineration or reuse (8).

An advanced degree of degradation of various types of solid or semi-solid waste into material suitable for reuse and/or discharge is achieved by adjusting the various flows in the system described above, taking into account the type of waste which is supplied, whereby a perfect process control is possible. The process and the apparatus are particularly suitable for the treatment of fruit, vegetables and garden waste.

EXAMPLE

A numerical comparison between the process according to the invention and A) a single-stage dry fermentation process of solid waste containing 40% of dry matter 60% of which is organic material, according to the prior art and B) a two-stage wet hydrolysis/fermentation process according to the prior art (such as EP 142.873) is given in Table I. The numbers are calculated on the basis of 25,000 tons of fruit, vegetable and garden waste annually. The three-stage process according to the invention is given in column C.

TABLE I

|  | A | B | C |
|---|---|---|---|
| Biogas production per ton of waste (Nm$^3$ CH$_4$/ton) | 68 | 50 | 80 |
| Reactor volumes (m$^3$) |  |  |  |
| * hydrolysis reactor | — | 2 × 500 | 2 × 500 |
| * RUDAD | — | — | 1 × 500 |
| * methane reactor | 2600 | 2 × 250 | 2 × 250 |
| Total (without buffer) | 2600 | 1500 | 2000 |
| Mass balance per ton of waste |  |  |  |
| amt. of water (l) | 360 | 360 | 360 |
| * amt. of anaerobic compost (kg) | 460 | 420 | 350 |
| * Required duration of aerobic post-treatment (days) | 5–14 | 5–14 | 1–4 |

The results given in table I show that the process according to the invention (C) is superior in the following respects:

it has the highest yield of biogas;
it has the lowest yield of residual solids;
it has the highest degree of degradation (best stabilization of the residues), resulting in the shortest post-treatment required.

Since the biogas production is a positive factor (energy production) and the solid residues are a negative factor (dumping), the process according to the invention is most cost-effective. Theoretically, a similar result could be obtained using a two-stage process including treatment with rumen derived flora and anaerobic fermentation as known e.g. from EP-150054, if the waste input were constant both in quantity and in composition, as explained above. Since this requirement is never met in practice, a comparison with such a two-stage process is not realistic.

We claim:

1. A three-stage process for the biological treatment of essentially solid organic material, wherein material is successively subjected to a biological hydrolysis treatment and anaerobic fermentation, which comprises: subjecting the material to the hydrolysis treatment by acidifying and hydrolyzing bacteria at a pH between 4.5 and 7.5; anaerobically treating at least a part of the solid material issuing from the hydrolysis treatment with at least a microorganism belonging to the rumen flora of ruminants; and anaerobically treating liquid material issuing from the hydrolysis treatment and liquid material issuing from the treatment with rumen microorganisms with methane forming bacteria.

2. A process according to claim 1, wherein the concentration of solids in the hydrolysis treatment is between 20 and 150 kg/m$^3$ and the concentration of solids in the treatment with rumen microorganism is between 40 and 120 kg/m$^3$.

3. A process according to claim 1, wherein, prior to the hydrolysis treatment, the material is diluted with liquid derived from the treatment with methane forming bacteria.

4. A process according to claim 1, wherein, prior to the hydrolysis treatment, the material is mechanically reduced in size to a particle size of no more than 15 mm and an average particle size of 1–5 mm.

5. A process according to claim 4, wherein a part of the solid material issuing from the hydrolysis treatment is recycled to at least one of the mechanical size reduction and the hydrolysis treatment.

6. A process according to claim 1, wherein a part of the solid material issuing from the treatment with rumen microorganisms is recycled to the treatment with rumen microorganisms.

7. A process according to claim 1, wherein a part of the liquid issuing from the treatment with methane forming bacteria is recycled to the treatment with rumen microorganisms.

8. A process according to claim 1, wherein the material is an organic waste.

* * * * *